United States Patent [19]
Kawagishi et al.

[11] Patent Number: 6,053,869
[45] Date of Patent: Apr. 25, 2000

[54] ULTRASOUND DIAGNOSTIC APPARATUS AND ULTRASOUND IMAGE PROCESSING APPARATUS

[75] Inventors: Tetsuya Kawagishi, Otawara; Yoshitaka Mine, Tochigi-ken, both of Japan

[73] Assignee: Kabushiki Kaisha Toshiba, Kawasaki, Japan

[21] Appl. No.: 09/200,888

[22] Filed: Nov. 27, 1998

[30] Foreign Application Priority Data

Nov. 28, 1997 [JP] Japan .................................. 9-328334

[51] Int. Cl.[7] ...................................................... A61B 8/00
[52] U.S. Cl. ............................................ 600/443; 600/455
[58] Field of Search ................................... 600/455, 445, 600/447, 437, 456

[56] References Cited

U.S. PATENT DOCUMENTS 5,615,680  4/1997  Sano .
5,622,174  4/1997  Yamazaki ................................ 600/455
5,800,356  9/1998  Criton et al. ........................... 600/455

FOREIGN PATENT DOCUMENTS 8-084729  4/1996  Japan .

OTHER PUBLICATIONS

A. Heimdal, et al., IEEE Ultrasonics Symposium Proc., pp. 1423–1426, Real–Time Strain Velocity Imaging (SVI), 1997.

A. Heimdal, et al., Journal of the American Society of Echocardiography, vol. 11, No. 11, pp. 1013–1019, "Real–Time Strain Rate Imaging of the Left Ventricle by Ultrasound", Nov. 1998.

*Primary Examiner*—Marvin M. Lateef
*Assistant Examiner*—Maulin Patel
*Attorney, Agent, or Firm*—Oblon, Spivak, McClellan, Maier & Neustadt, P.C.

[57] ABSTRACT

By scanning a cross-section of an inside of a subject through an organ of interest with an ultrasonic wave it is possible to generate tissue cross-sectional data relating to the cross-section and motion velocity data relating to the region of interest. The motion velocity data is comprised of transmit/receive direction components of the ultrasonic wave. In order to obtain a motion velocity, or its near-motion velocity, of a direction of interest, it is necessary to angle-compensate the motion velocity data in accordance with a given direction of interest. According to the present invention, the direction-of-interest necessary to effect the angle compensation is assumed based on the contour of the organ of interest which can be extracted from the tissue cross-sectional data.

19 Claims, 7 Drawing Sheets

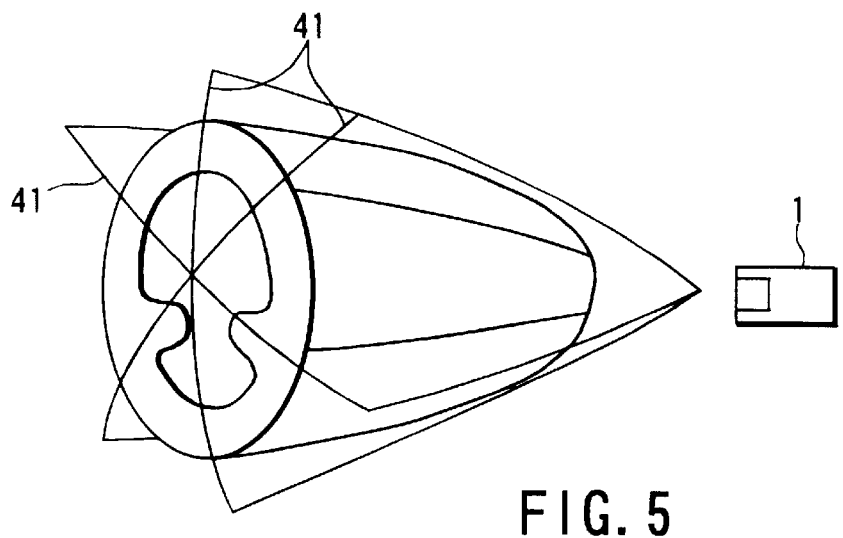
FIG. 5
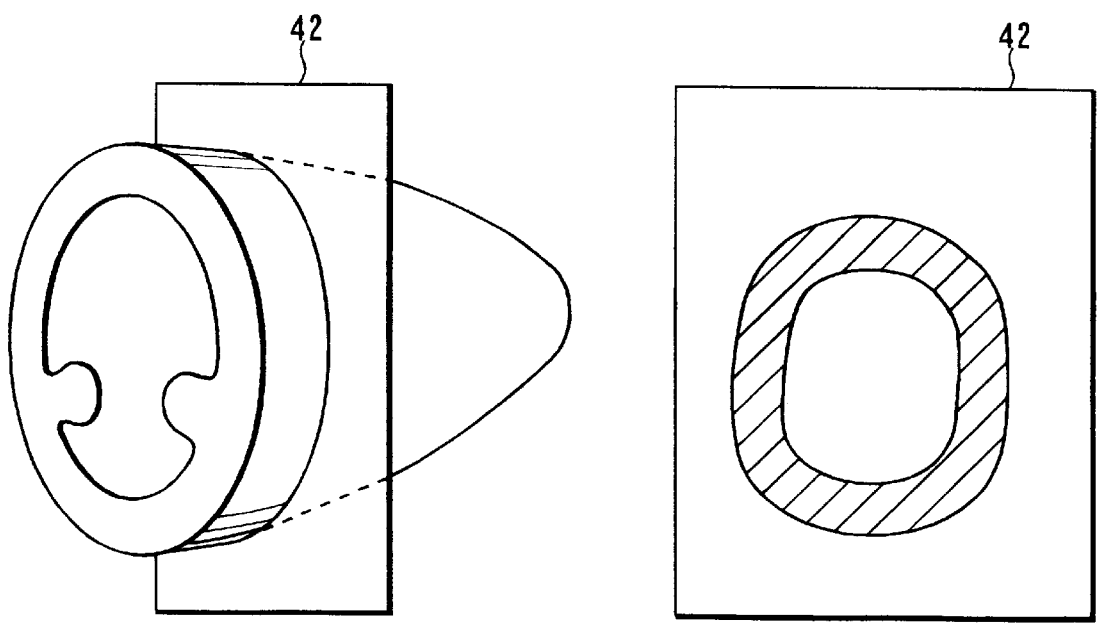 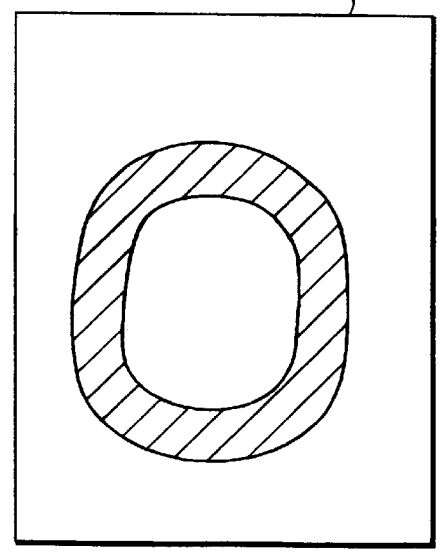
FIG. 6A　　　　　　　　FIG. 6B

ULTRASOUND DIAGNOSTIC APPARATUS AND ULTRASOUND IMAGE PROCESSING APPARATUS

BACKGROUND OF THE INVENTION

The present invention relates to an ultrasound diagnostic apparatus for calculating a functional index from a motion rate of a cardiac muscle and ultrasound image processing apparatus.

An objective and quantitative evaluation of a cardiac motion, that is, contracting and dilating motions, is very important to the heart diseases. As the quantitative evaluation method there are the left-ventricular wall motion analytic method, stress echo method, etc. However, the left-ventricular wall motion analytic method, etc., is one special to ischemic cardiac diseases and has no general applicability.

Further, the left-ventricular wall motion analytic method comprises finding a cardiac muscle thickness from a tissue cross-sectional image (B-mode image) and calculating a temporal variation in the cardiac muscle thickness and provides no objective basis. Further, the left-ventricular motion analytic method cannot calculate the index relating to the longitudinal-axis direction of the heart.

Such a problem can be solve by what is called a segment shortening method. This method comprises embedding a plurality of strong reflectors (for example, crystals) in the cardiac muscle and very much highly accurately measuring the motion function of the heart by tracing the positions of these strong reflectors. This segment shortening method is highly dangerous and has been thought impossible to apply it to a human being. In the present time, it may be said that there is no method for measuring the motion function of the heart with a precision equal to that of the segment shortening method.

In order to measure the motion function of the heart with high precision, it is very important to investigate the motion directions (contracting and dilating directions) of the heart. These motion directions not only differ in each part of the heart but also constantly vary in the same part. It is, therefore, impossible to measure the motion function of the heart very accurately.

BRIEF SUMMARY OF THE INVENTION

The object of the present invention is to provide an ultrasound diagnostic apparatus and ultrasound image processing apparatus which can highly accurately measure an index on a local cardiac function.

According to the present invention, it is possible to generate tissue cross-sectional image data relating to a cross-section and motion velocity data relating to an organ of interest by scanning the cross-section of an inside of a subject through the organ of interest with an ultrasonic wave. The motion velocity data is comprised of transmit/receive direction components of the ultrasonic wave. In order to obtain a motion velocity data of a direction of interest or its near-motion velocity, it is necessary to angle-compensate the motion velocity data in accordance with the motion direction of the organ of interest. According to the present invention, the motion direction of the organ of interest necessary to the angle compensation is assumed from the outline of the organ of interest extractable from the tissue cross-sectional data and it is done so without requiring any cumbersome operation on the part of the operator. It is possible to highly accurately measure the cardiac function's index from the motion velocity of the assumed direction.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 5 is a view showing a 3-dimensional scanning method with the use of a cardiac apex approach;

FIG. 6A is a view showing a 3-dimensional map of an index calculated by the index processor in FIG. 1;

FIG. 6B is a view showing a 2-dimensional map of an index relating to a cross-section in FIG. 6A;

DETAILED DESCRIPTION OF THE INVENTION

Figure 1:
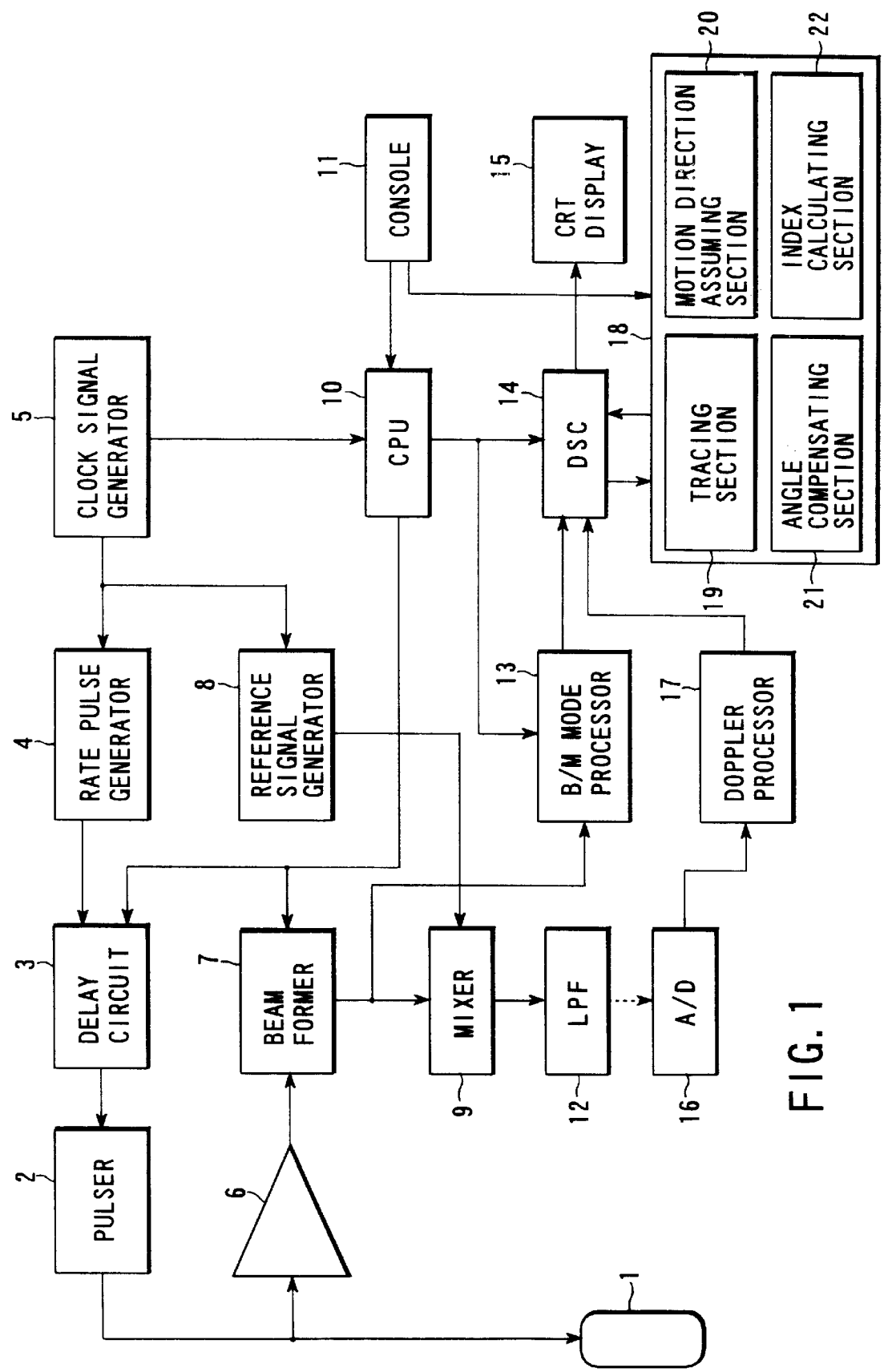
FIG. 1 is a view showing a arrangement of an ultrasound diagnostic apparatus according to a preferred embodiment of the present invention.

A preferred embodiment of the present invention will be explained below in more detail with reference to the drawing.

FIG. 1 shows an arrangement of an ultrasound diagnostic apparatus of the present invention. A clock pulse is output from a clock pulse generator 5 and supplied to a rate pulse generator 4 where it is frequency divided to a rate pulse. The rate pulse is fed past a transmit delay circuit 3 and, as a trigger, to a transmit pulser 2. The transmit pulse generator 2 repeatedly applies a short-length pulse voltage of a given center frequency f0 to an array vibrator-equipped probe 1 in synchronism with the rate pulse. It is to be noted that the transmit/receive period is given as a reciprocal of the rate frequency. The transmit delay circuit 3 controls a timing of a transmit pulse voltage applied to a plurality of vibration elements to allow a variation in direction of the ultrasound beam and focusing of the beam. This is hereinafter referred to as a beam forming. The ultrasound pulse radiated from the probe 1 into the human body and echoed on a discontinuous plane of an acoustic impedance in the human tissue is received by the same probe 1. Those received signals are amplified by a pre-amplifier 6 and received at a receive delay circuit 7 where they are additively formed. This is what is called "beam forming" processing. Through this processing, an echo signal is generated, having a directivity with an echo component from one direction being enhanced.

The echo signal is envelop-detected by a B/M mode processor 13 and converted to an amplitude signal. The amplitude signal is supplied to a digital scan converter (DSC) 14 where it is formed to a B mode image representing a tissue form. The B mode image is displayed on a CRT display 15.

The echo signal is supplied to a mixer 9 where it is multiplied by a reference signal of the same frequency as a transmit frequency, that is, a reference signal supplied from a reference signal generator 8. The signal from the mixer 9 is supplied to a lowpass filter 12 where it is filtered. This processing is what is called an orthogonal phase detection by which a frequency component shifted due to a Doppler effect is extracted from the echo signal. The extracted signal is referred to as a Doppler signal. The Doppler signal is converted by an analog/digital (A/D) converter 16 to a digital signal and supplied to a Doppler processor 17.

The Doppler processor 17 performs processing on the Doppler signal in accordance with the tissue Doppler imaging method. By this processing, the motion rates of the tissue such as the cardiac muscle are calculated at its sampling points (hereinafter referred to simply as "points") in the scanning range of the ultrasonic beam to enable the rate information to be generated as a two-dimensional speed distribution (tissue Doppler image) by the digital scan converter 14. The two-dimensional speed distribution is displayed in color on a CRT display. It is to be noted that the signal processing by the tissue Doppler imaging method is basically the same as that by a color flow Doppler imaging (CFM) method. That is, this comprises, by passing a Doppler signal through a bandpass filter called an MTI, extracting a specific frequency component, frequency-analizing the extracted signal by an autocorrector at high speeds and calculating an average speed, etc., by a calculator on the basis of its analytical result. The passband of the bandpass filter is set, at the CFM time, to a relatively high frequency region in accordance with the bloodstream rate and at a tissue Doppler imaging time, to a relatively low frequency region in accordance with the cardiac motion rate.

An index calculation unit 18 calculates an index, at each point or each local area (divided area) with the use of a B mode image and tissue Doppler image, the index providing data for determining a normal/abnormal state of a motion function of the tissue such as the cardiac muscle. The calculated index is sent through the DSC 14 to the CRT display 15.

The processing by the index calculation unit 18 relating to the index calculation is achieved by a hardware or software. Probably the software is thought advantageous and, in this case, the processing relating to the later-described index calculation can be implemented by a computer, that is, by a program code programmed in a computer-readable storage medium, such as a floppy disk, magnetic disk and optical magnetic disk. In FIG. 1, the index calculation unit 18 comprises a tracing section 19, motion direction assuming section 20, angle compensating section 21 and index calculating section 22. These sections may correspond to a hardware unit for performing their allocated processing in the case of making processing relating to the index calculation and correspond to a program code for performing their allocated processing, or a program code section, in the case of realizing them with the software.

The featuring portions of the present embodiment will be explained in more detail below.

Figure 2A:
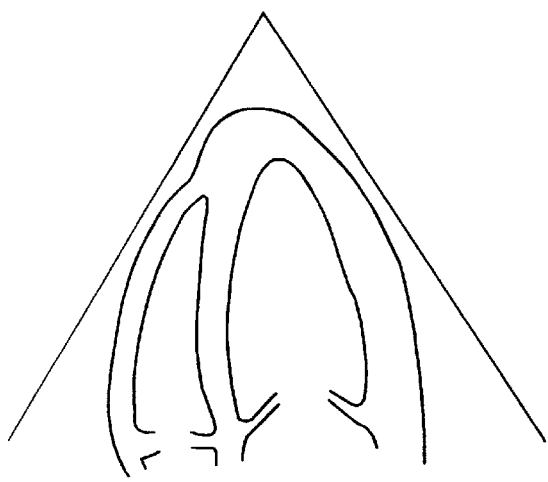
FIG. 2A shows a longitudinal axis section image of the heart which is generated on a B/M mode processor.

FIG. 2A is a model diagram showing a longitudinal axis section image (tissue's configuration image) of the left ventricle of the heart obtained through a cardiac apex approach. It is assumed that the longitudinal axis sectional image is taken by the ultrasound diagnostic apparatus to obtain a two-dimensional speed distribution (tissue's Doppler image) of a cardiac muscle tissue on the cross-sectional area by the tissue's Doppler imaging (TDI).

Here, it is necessary for a found index to be effective to the diagnosis of the motion function of the cardiac muscle and it is desirable to have a significance equivalent in clinical diagnosis to that of a "segment shortening" confirmed by animal experiments, etc., for its effectiveness. That is, if the cardiac muscle is contracted or dilated in a given direction on the longitudinal axis section image, an index to be found becomes a nonzero value.

It is required that the positive and negative values of the index value represent a contraction or dilation and the magnitude of the index value reflect the extent of contraction and dilation. It may be considered that there are a velocity difference, velocity gradient, velocity differentiation, etc., as an index for satisfying such needs.

Of importance to calculate the index is how the motion direction should be predicted when handling it on calculation. The velocity obtained by the tissues Doppler imaging is, as well known, simply a velocity component of the ultrasonic beam direction. It is necessary that, in order to obtain a velocity, or near-velocity, of a motion direction of interest, the velocity obtained in the tissue's Doppler imaging be compensated by an angle of the ultrasonic beam made with respect to the cardiac muscle's motion direction. That is, the nearer the motion direction is to the cardiac muscle's motion direction of interest, the higher the compensation precision and hence the index precision becomes. According to the present embodiment, this motion direction is predicted based on the outline of the cardiac muscle.

Figure 2B:
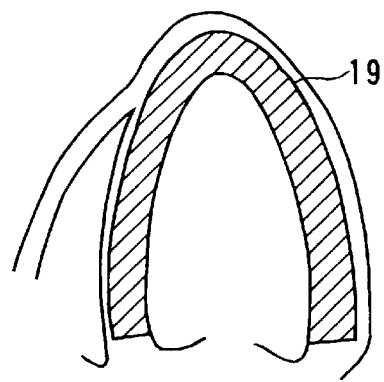
FIG. 2B is a view showing an outline of a cardiac muscle traced by a tracing section in FIG. 1.

First, the cardiac muscles outline on the longitudinal axis sectional image of the left ventricle is traced either by a manual operation by using a console 11 such as a track ball while receiving a support of the tracing section 19 or by an automatic operation. The tracing of the cardiac muscles outline may be effected by tracing an endocardium and epicardium or a simpler method may be used by which discrete points designated on the endocardium and epicardium are connected either by straight lines or by a curve approximation. As a complete automatic method it may be possible to extract a cardiac cavity/cardiac muscle outline based on a luminance gradient and do this with the use of a procedure such as an ACT method. A cardiac muscle's area defined by this trace is handled as a region 19 of interest (FIG. 2B).

In the motion direction assuming section 20, the direction tracing the endocardium 20 (or epicardium), such as a tangent line direction, is assumed as a motion direction with a plurality of points on the traced cardiac muscle region 19 being as a target. In the angle compensating section 21, the motion velocities at a plurality of points in the cardiac muscle region 19 in the tissue Doppler image are angle-compensated, as follows, based on the assumed motion direction.

The motion direction assuming section 20 is not restricted to the tangent line direction and the motion direction may be assumed from other extraction methods. For example, the motion direction may be assumed so that the absolute value of the index may become maximal.

Figure 2C:
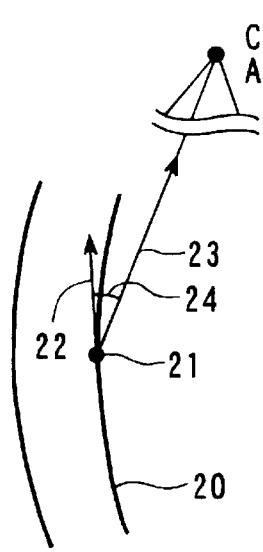
FIG. 2C is a view showing a motion direction at a point on a cardiac muscle's endocardium assumed by a motion direction assuming section with the use of the outline of the cardiac muscle in FIG. 2B.

As well known, the Doppler method is not restricted to the TDI and the velocity data to be measured corresponds to the velocity component of the ultrasonic beam direction. As shown in FIG. 2C, the velocity V at a point 21 on the endocardium line 20 is angle-compensated by "V/cos θ" with the use of a vector 22 contacting with the local endocardium line at a point 21 and an angle (θ) 24 made with respect to a vector 23 representing a sense of the ultrasonic beam. By doing so it is possible to obtain a velocity component in a direction of the vector 22.

Figure 2D:
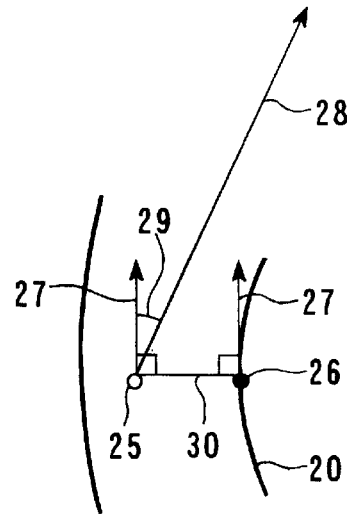
FIG. 2D is a view showing a motion direction of an inside of the cardiac muscle assumed by the motion direction assuming section with the use of the outline of the cardiac heart in FIG. 2B.

As shown in FIG. 2D, at an inner point 25 of the cardiac muscle region 19 which is not on the endocardium line 20, a motion direction assumed at a crosspoint 26 between a vertical drawn from the point 25 to the endocardium 20 and the endocardium 20 is applied and, with the use of an angle 29 of a vector 27 of that motion direction made with respect to a vector 28 representing a sense of the ultrasonic beam at the point 25, the velocity at the point 25 is angle-compensated as in the above-mentioned case.

Figure 2E:
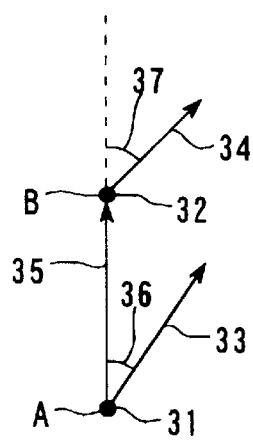
FIG. 2E is a supplementary view relating to a calculation on a velocity gradient (index) at a point-to-point area which is done by the index calculation section in FIG. 2E.

The index calculation method by the index calculating section 22 will be explained below. As shown in FIG. 2E, two points in the cardiac muscle region 19 are given as A and B and velocity data VA and VB at their respective points before the angular compensation are given as VA and VB. In this connection it is to be noted that the VA shows a velocity at the point A measured by the TDI method and the VB a velocity at the point B measured by the TDI. A velocity component of a direction following the cardiac muscle at the point A is given as VAx, a velocity component of a direction following the cardiac muscle at the point B is as VBx, a velocity component of a direction orthogonal to the cardiac muscle or the endocardium at the point A is as VAx and a velocity component of a direction orthogonal to the cardiac muscle at the point B as VBy. AB represents a position vector of the B with the point A set as an origin. θA represents an angle made between a direction toward the ultrasonic probe and a direction following the cardiac muscle at the point A and θB represents an angle made between a direction toward the ultrasonic probe and a direction following the cardiac muscle at the point B. At the time, the respective factors are as follows:

$$|\text{velocity gradient}| = |VAx - VBx|/|AB|$$

$$VA = VAx \cdot \cos\theta A + VAy \cdot \sin\theta A$$

$$VB = VBx \cdot \cos\theta A + VBy \cdot \sin\theta B$$

At this time, when the points A and B are near to each other, $$\theta \equiv \theta A \approx \theta B \text{ and}$$

$$VAy \approx VBy$$

and the velocity gradient can be expressed as follows:

$$|\text{velocity gradient}| = |VA - VB|/(|AB| \cdot \cos\theta)$$

The index calculation unit 18 finds the velocity gradient from the above-mentioned equation for instance and outputs it as the index. It is to be noted that, since an increase of a θ value leads to an increase of an error resulting from the angle compensation, the θ is set as being immeasurable in the case of the θ value exceeding a predetermined value and the velocity gradient value is not displayed. The velocities VA, VB are given as a positive value if their respective points move in a direction toward the probe and as a negative value if their points move in a direction away from the probe. The positive and negative values of the velocity gradient output from the index calculation unit 18 are so arranged that, taking the coordinate of the points A and B into consideration, it takes a positive value if the cardiac muscle is dilated between the points A and B and a negative value if the cardiac muscle is contracted. It is to be noted that the positive and negative values of the velocity gradient are so arranged as to take a negative value when the cardiac muscle is dilated and a positive value when the cardiac muscle is contracted. Further, the absolute value of the velocity gradient corresponds to the magnitude of a dilation percentage.

If this calculation is made between the two adjacent points, it can be taken as a velocity difference and, if the distance between the two adjacent points is very small, it can be taken as a velocity differentiation. The velocity gradient may be found as an inclination by performing a "straight line fitting" by a least-squares method from a profile of all angle-corrected velocity data between the two points. By the sign of the index thus found it is possible to know the contraction or dilation of the tissue. By the magnitude of the index it is also possible to find the extent of the contraction and dilation.

Figure 3A:
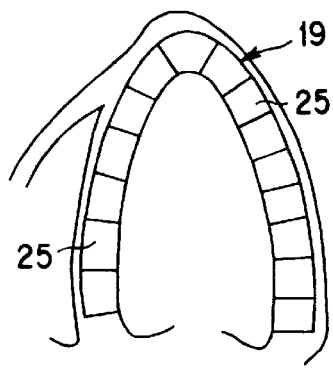
FIG. 3A is a view showing division segments divided by the index calculating section.
Figure 3B:
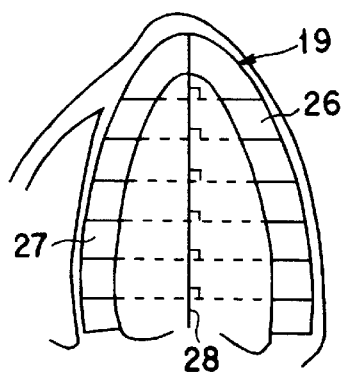
FIG. 3B is a view showing additional division segments divided by the index calculating section in FIG. 1.
Figure 3C:
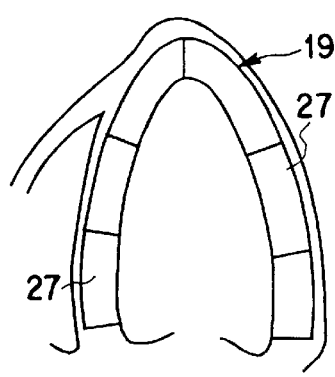
FIG. 3C is a view showing further additional division segments divided by the index calculating section in FIG. 1.

The index may be found at respective points in the region of interest. As shown in FIGS. 3A, 3B and 3C, the cardiac muscle's region 19 is divided into a plurality of local segments 25, 26, 27 and by doing so, the index may be found one by one for each local segment. The local segments may be overlapped with each other. The cardiac muscle's region may be divided as follows. That is, as shown in FIG. 3A, a plurality of verticals are drawn at equal distances onto the endocardium and, by doing so, the cardiac muscle's region 19 may be divided by the verticals into a plurality of local segments. As shown in FIG. 3B, the cardiac muscle's region may be divided into a plurality of local segments 27 by verticals drawn at equal intervals onto the longitudinal axis 28. As shown in FIG. 3C, the cardiac muscle's region may be divided into local segments 27 recommend by ASE (American Society of Echocardiography) and, by doing so, the index may be calculated for each segment.

In the case where the region (cardiac muscle's region) of interest is divided, it may be considered that the index is found by the above-mentioned equation from the average value, etc., of those velocities at a plurality of points in the respective divided segments. In this case, it can be expected that it is possible to obtain the advantage of eliminating noise, such as a variation resulting from a result of calculation.

It is to be noted that the motion direction of the cardiac muscle may be not only toward the tangent line of the cardiac muscle's endocardium (or epicardium) as set out above but also be so unified as to be made, at all points, parallel to the longitudinal axis direction of the heart. In either case it can be expected that, under the velocity assumption by the TDI, measurement is highly accurately made at a smaller Doppler angle through a cardiac apex approach or a through-the-esophagus approach.

A plurality of angle-compensated velocity data on the vertical 30 are, for example, averaged and the average value, etc., is handled as a represented one. By doing so, it can be taken as the velocity data on the point 26 on the endocardium line. Further, the region of interest may be not only the cardiac muscle but also the endocardium or epicardium. In this case, as the velocity data use may be make of data on the endocardium or epicardium or its neighborhood.

Figure 4A:
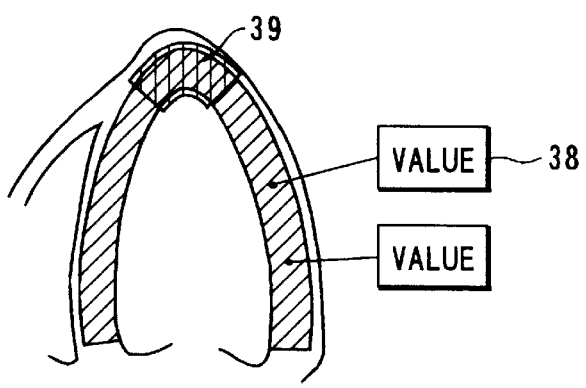
FIG. 4A is a view showing a 2-dimensional map of an index calculated at each point by the index calculating section in FIG. 1.
Figure 4B:
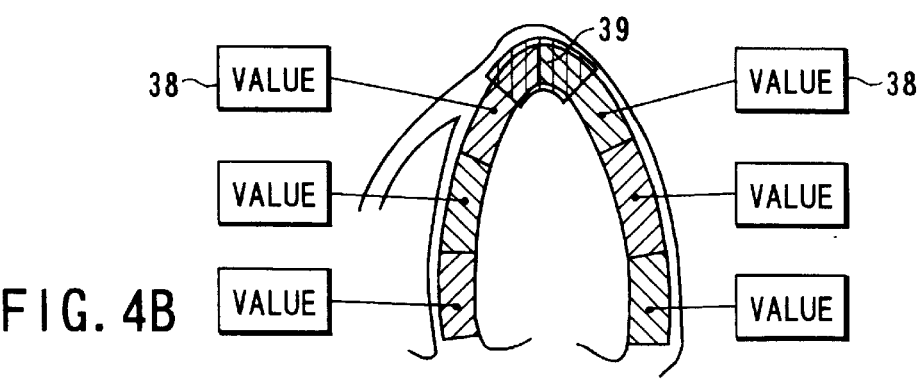
FIG. 4B is a view showing a 2-dimensional map of an index calculated at each division segment by the index processor in FIG. 1.

As the display method for displaying the index calculated by the index calculation unit 18, the two-dimensional distribution (index map) of the index is color-displayed in a hue corresponding to its value as shown in FIGS. 4A and 4B and by doing so it is easier to grasp a spatial variation of the cardiac motion function. The color display is done in a red-color system in the case of the cardiac muscle being contracted in a direction, etc., toward contacting with the endocardium, etc., and in a blue color system in the case of the cardiac muscle being dilated. Further, various color display methods may be considered such as by the giving of a color in accordance with the absolute value of the index. It is also important to display the index value, per se, directly by the value 38. The color display and value display may be made in a way to be superimposed on the region-of-interest on a image or be made in other portions.

Theoretically, it is desirable to calculate the index, with adequate precision, relating to all portions on a cross-sectional image. Since, however, an angle between the calculation direction of the index (the compensation direction of the velocity) and the ultrasonic beam direction involves a greater angle-compensation error at an area exceeding a predetermined angle near to the vertical, it is desirable that such an area be detected by the index calculation unit 18 as being immeasurable and be displayed in a different system of color or as being free from any index color. By doing so, it is possible to avoid any danger of a wrong diagnosis from an area involving a possibility of having a greater error. In the case where the region of interest is divided as shown in FIGS. 3A, 3B, 3C, if there exits any immeasurable segment, it is only necessary to calculate the index of the divided segments from the velocity data of points in a range except for that segment.

Heretofore, an explanation has been explained about the 2-dimensional evaluation of the heart's motion function. In the cardiac apex approach and through-the esophagus approach, scanning is repeated with the ultrasonic wave while rotating the probe 1, for example, around the longitudinal axis of the heart's left ventricle and it is possible to acquire a 3-dimensional configuration information (tissue cross-sectional image) and velocity information (tissue Doppler image) over the whole of the heart. The probe may be swung, in a circular arc way, over a scanning surface or be moved in a parallel way. By calculating the index with the use of the acquired tissue cross-sectional image and tissue Doppler image and interpolating intervals on the scanning surface it becomes possible to obtain the index representing the local heart's motion function over the heart.

Needless to say, the index may be calculated after an interpolation of velocity data. If the information on the whole of the heart's left ventricle thus obtained is displayed as a normal 3-dimensional image and further any given cross-section is cut as shown in FIG. 6, it is possible to easily grasp, in a 3-dimensional way, how far, for example, an infarction region extends.

Further, if a bull's eye map as used in the nuclear medicine, that is a developed view as seen from the inside of the heart, is prepared and displaced, it is possible to display the 3-dimensional information of the heart one at a time.

Figure 7A:
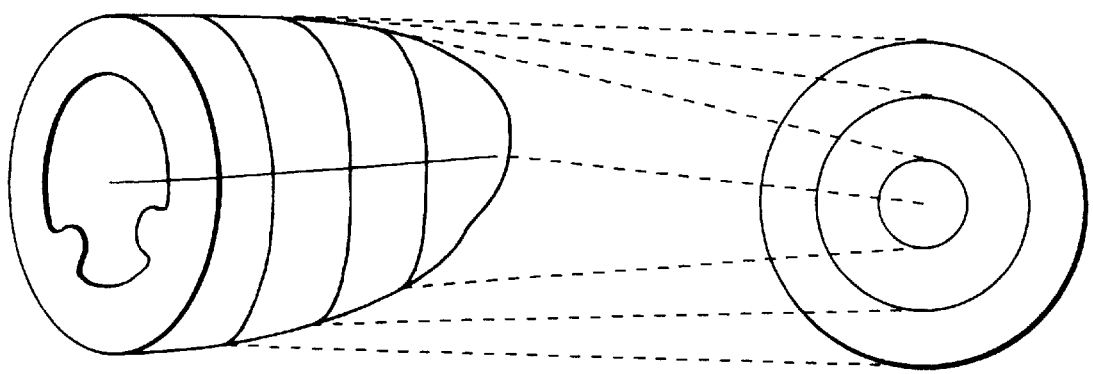
FIG. 7A is a view showing a bull's eye map of an index calculated by the index processor in FIG. 1.
Figure 7B:
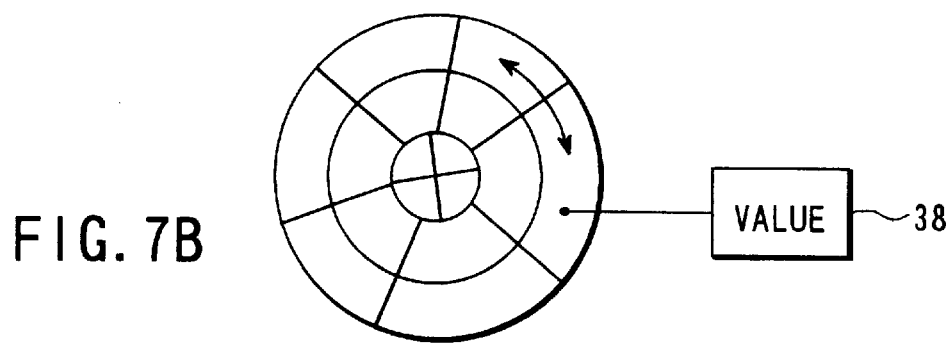
FIG. 7B is a view showing a bull's eye map of an index calculated at each division map by the index processor in FIG. 1.
Figure 7C:
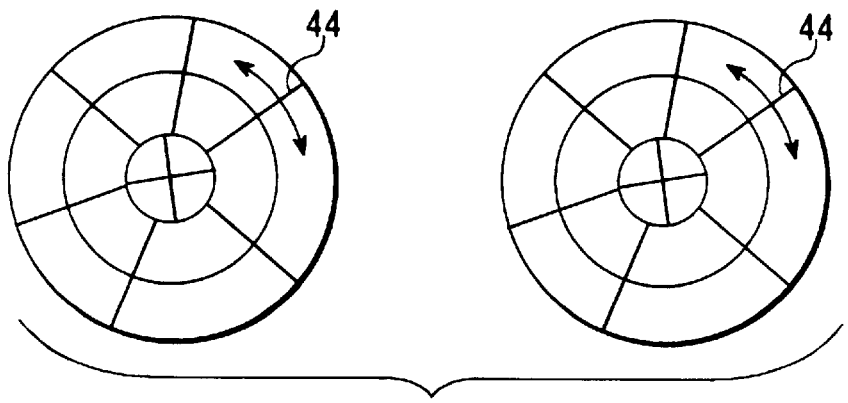
FIG. 7C is a view showing a parallel display array form of a bull's eye map of an index calculated at each point by the index processor in FIG. 1 and a bull's eye map of an index calculated at each division segment by the index processor in FIG. 1.

As shown in FIG. 7B, if the index at each divided segment is displayed by the bull's eye map, the motion function of the heart is distinguished for each dominant segment of the respective coronary artery. It is expected that, in a boundary area, etc., of a diminished motion function of the heart, the index value of the individual divided segment is affected depending upon how the divided segment should be set. There, both the index maps obtained by being divided into segments and by not being divided into segment's are displayed one at a time, or they are displayed in a parallel array and segment division lines are guide-displayed as shown in FIG. 7C and linked to each other in such a manner that, when one is moved while, at the same time, the other is moved. By doing so it is possible to effect an optimal segment division. At this time it is desirable to re-calculate the index of the respective division ratio, in realtime, in accordance with the movement of the segment division line 44 and display it.

Although, as set out above, the motion direction of the heart has been explained as being assumed in a direction tangent to the inner and epicardiums of the cardiac muscle, this has a connotation that the derivation of such a tangent direction from the region of interest can produce a complete automation and save a lot of time and labor of the operator.

It is considered that, for the case of the heart's short-axis image, the measurement velocities are angle-compensated in a direction from each point of the cardiac muscle toward the center of gravity and, by doing so, an index relating to the wall thickness is calculated. Hereinafter, this method will be explained below.

Figure 8A:
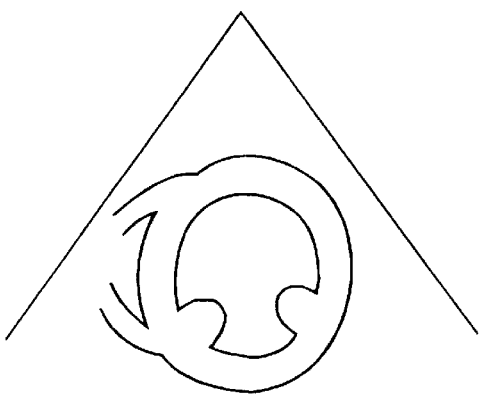
FIG. 8A is a view showing a short-axis sectional image of the heart produced by a B/M mode processor in FIG. 1.
Figure 8B:
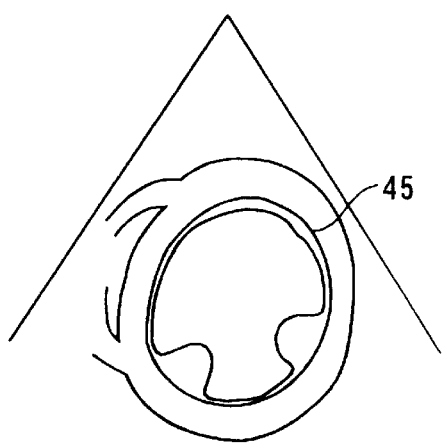
FIG. 8B is a view showing an outline of the cardiac muscle traced by a tracing section in FIG. 1.

FIG. 8A is a model view showing a short-axis cross-sectional image of the heart's left ventricle. It is assumed that this image is displayed on a CRT display 15. The endocardium 45 of the cardiac muscle of the left ventricle's short-axis cross-sectional image is traced by the processing of the section 19 and the manual operation of the console 11 (see FIG. 8B). As a tracing method, either the endocardium may be traced or a simpler method may be used by which, if the operator designates some points discretely on the endocardium, these points are connected together by a straight line or by a curve approximation. Further, as a complete automation method, a cardiac cavity/cardiac muscle boundary may be derived, based on the luminance gradient, with the use of the technique such as the ACT method. The epicardium 46 may be traced as in the case of the endocardium or either a curve spaced a predetermined distance from each point on the endocardium may be handled as the epicardium or the epicardium may be handled as an enlarged similar one to the configuration of endocardium.

Figure 8C:
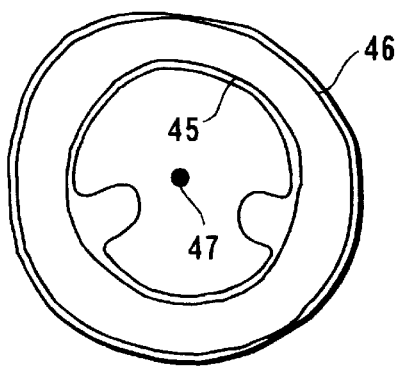
FIG. 8C is a view showing a center of gravity of the cardiac muscle specified by the motion direction assuming section in FIG. 1 with the use of the outline in FIG. 8B.
Figure 8D:
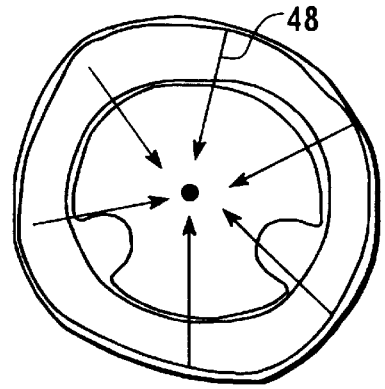
FIG. 8D is a view showing a motion direction of the cardiac muscle assumed by the motion direction assuming section in FIG. 1 with the use of the center of gravity in FIG. 8D.

When the endocardium and epicardium are thus traced, the assuming section 20 either calculates the center-of-gravity position from an outline coordinate of the inner and epicardium or specifies the center of gravity, 47, from an area center of gravity, etc., of a cardiac muscle portion at the endocardium and epicardium (FIG. 8C). At respective points of the cardiac muscle at the region of interest, motion directions are assumed in those center-of gravity orienting directions (FIG. 8D).

Figure 8E:
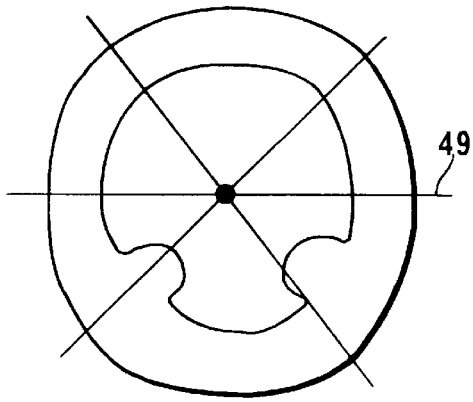
FIG. 8E is a view showing a method for dividing the cardiac muscle by the index calculating section in FIG. 1.
Figure 8F:
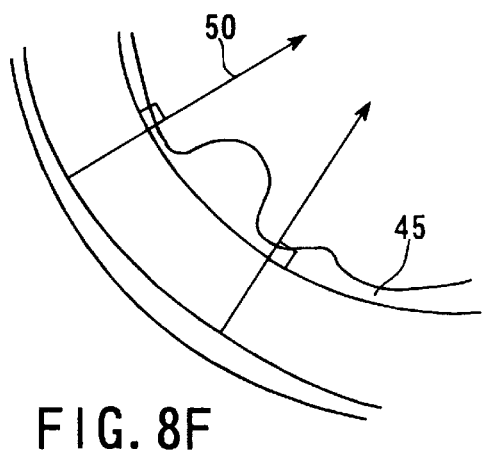
FIG. 8F is a view showing a thickness direction of the cardiac muscle.
Figure 9:
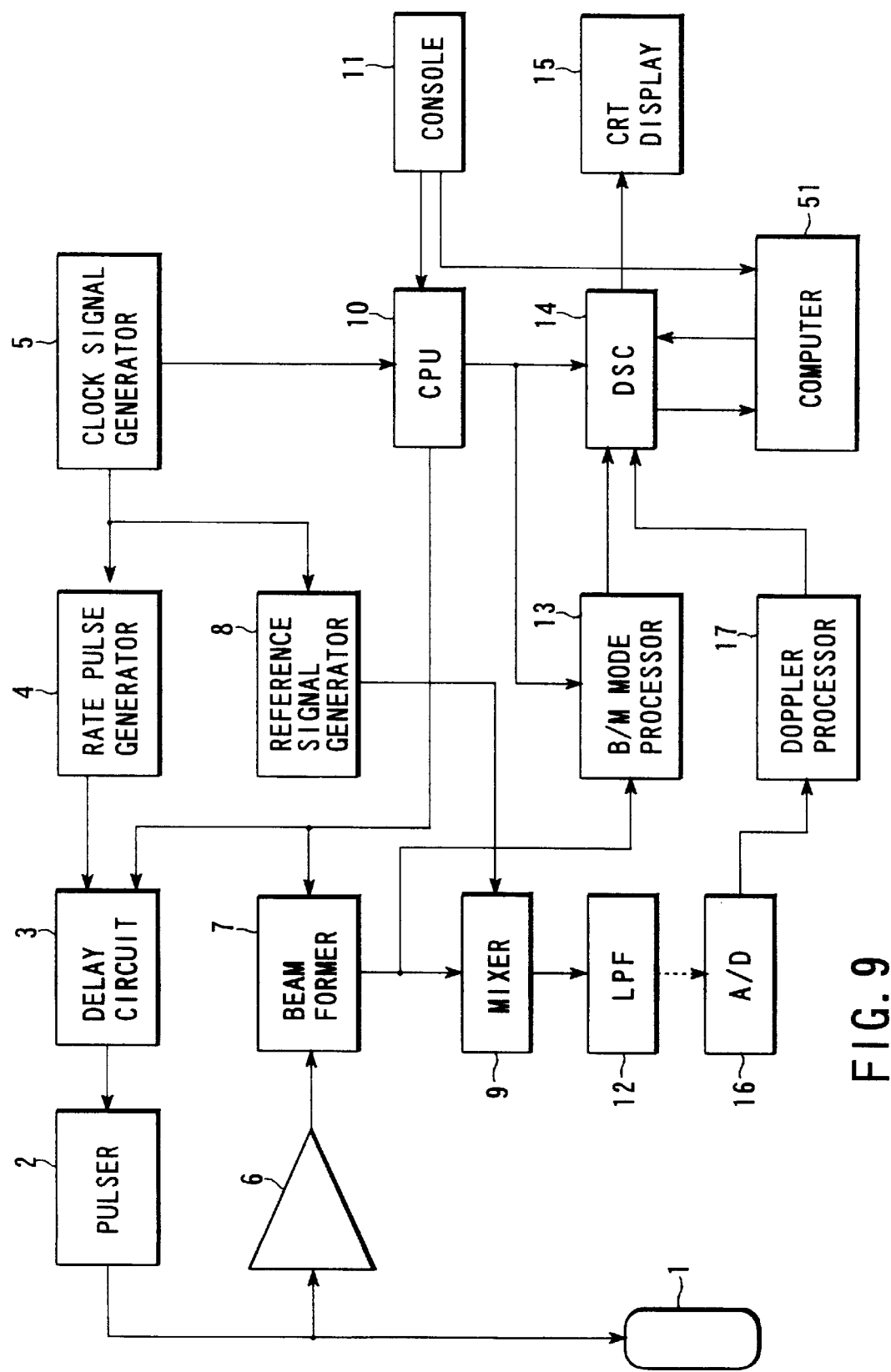
FIG. 9 is a block diagram relating to a variant of the present invention.

Even upon dividing the region of interest into those segments recommended by the ASE, it is possible to automatically draw a plurality of division lines 49 by drawing these division lines 49 in a radial way with a center of a center-of-gravity set as a center and it is possible to save a lot of time and labor (FIG. 8E). Further, in the case where the index of the thickness direction of the cardiac muscle is to be calculated, it is only necessary to find those directions normal to the curve of the endocardium at each part of the traced endocardium as shown in FIG. 8F. After the setting of the direction it is only necessary to calculate the velocity difference, velocity gradient, velocity differentiation and velocity difference. In this case, these indexes are related to the wall-thickness variation velocities.

Since the velocity is angle-compensated by the motion direction assumed based on the outline of the region of interest and the index representing the dilation function of the cardiac muscle is calculated from the angle-compensated velocity, it is possible to improve the accuracy of the index. Further, since the operator simply participates in tracing the region-of-interest of the cardiac muscle, etc., this places no burden on the operator. If the motion direction can be displayed and adjusted at any given point in the region of interest, then the operator can confirm the motion direction assumed by the index calculation unit 18 and make a proper minor correction. After the minor correction, the index calculation unit 18 angle-corrects the velocity based in the minor-corrected motion direction and the index is calculated.

It is to be noted that the setting of the region of interest, calculation and display, etc., of the index can be done, separate from the ultrasound diagnostic apparatus, by a computer 51 such as a personal computer and workstation equipped with the functions of the measurement processing sections FIG. 1. The data such as the B mode image, tissue Doppler image, etc., output from the DSC 14 are sent to the computer 51 and results of calculation may be displaced on a monitor attached to the computer or on a CRT 15 of the diagnostic apparatus.

As already set out above, the index on the motion function of, for example, the heart can be evaluated simply, objectively and quantitatively and provides information useful to the diagnosis.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

We claim:
1. An ultrasound diagnostic apparatus comprising:
   means for scanning a cross-sectional surface of an inside of a subject with an ultrasound, the cross-sectional surface crossing an organ-of-interest of the subject;
   means for, based on a received signal obtained through the scanning, generating a tissue cross-sectional image relating to the cross-sectional surface;
   means for, based on the received signal obtained through the scanning, generating motion velocity data relating to the organ-of-interest;
   means for extracting an outline of the region-of-organ from the tissue cross-sectional image data;
   means for assuming a motion direction of the organ-of-interest based on the outline of the organ-of-interest; and
   means for compensating the motion velocity data based on the assumed motion direction.

2. The ultrasound diagnostic apparatus according to claim 1, further comprising means for, based on the compensated motion velocity data, calculating an index representing a motion function of the organ-of-interest.

3. The ultrasound diagnostic apparatus according to claim 1, wherein the assuming means assumes the motion direction in a direction tangent to the outline of the organ-of-interest.

4. The ultrasound diagnostic apparatus according to claim 1, wherein the assuming means assumes the motion direction normal to the outline of the organ-of-interest.

5. The ultrasound diagnostic apparatus according to claim 1, wherein the assuming means assumes the motion direction in a direction toward a center-of-gravity of the outline of the organ-of-interest.

6. The ultrasound diagnostic apparatus according to claim 1, wherein the assuming means assumes the motion direction so as to allow an absolute value of the index to become maximal.

7. The ultrasound diagnostic apparatus according to claim 1, wherein the organ-of-interest is the heart and the assuming means assumes the motion direction in such a way as to follow the outline of the heart's endocardium or epicardium.

8. The ultrasound diagnostic apparatus according to claim 1, wherein the compensating means compensates the motion velocity data based on an angle made between the assumed motion direction and an ultrasonic beam.

9. The ultrasound diagnostic apparatus according to claim 1, further comprising means for displaying an angle made between the assumed motion direction and an ultrasonic beam.

10. The ultrasound diagnostic apparatus according to claim 1, further comprising means for color-displaying an angle made between the assumed motion direction and an ultrasonic beam in a way to be superimposed on the tissue cross-sectional image.

11. The ultrasound diagnostic apparatus according to claim 2, further comprising means for displaying the calculated index in 2-or 3-dimensional way.

12. The ultrasound diagnostic apparatus according to claim 11, wherein the index displaying means displays the index in a color corresponding to an index value.

13. The ultrasound diagnostic apparatus according to claim 2, wherein the index calculating means calculates the index at each of a plurality of segments into which the region-of-interest is divided.

14. The ultrasound diagnostic apparatus according to claim 13, wherein the assuming means assumes motion directions one by one at each divided segment.

15. An ultrasound image processing apparatus comprising:

means for entering tissue cross-sectional image data relating to a cross-section of an inside of a subject and motion velocity data relating to an organ-of-interest in the subject;

means for extracting an outline of the organ-of-interest from the tissue cross-sectional image data;

means for assuming a motion direction of the organ-of-interest based on the outline of the organ-of-interest; and means for compensating the motion velocity data based on the assumed motion direction.

16. An ultrasound diagnostic apparatus comprising:

means for scanning a cross-section of an inside of a subject, the cross-section crossing an organ-of-interest;

means for, based on a received signal obtained through the scanning, generating tissue cross-sectional image data relating to the cross-section;

means for, based on the received signal obtained through the scanning, generating velocity data relating to a direction in which the ultrasonic wave is transmitted and received; and means for calculating motion velocity data relating to the motion direction of the organ-of-interest from the tissue cross-sectional image data and velocity data.

17. An ultrasound diagnostic apparatus comprising:

means for scanning a cross-section of an inside of a subject, the cross-section crossing an organ-of-interest;

means for, based on a received signal obtained through the scanning, generating a tissue cross-sectional image data relating to the cross-section;

means for, based on the received signal obtained through the scanning, generating velocity data relating to a direction in which an ultrasonic wave is transmitted and received; and means for calculating motion velocity data relating to a motion direction of the organ-of-interest from both an outline of the organ-of-interest obtained from the tissue cross-sectional image data and velocity data.

18. An ultrasound diagnostic apparatus comprising:

means for scanning an inside of a subject with an ultrasonic wave;

means for generating a cardiac muscle's cross-sectional data based on a received signal which is obtained through the scanning;

means for generating motion velocity data on a direction tangent to a contour of the cardiac muscle on the basis of the received signal which is obtained through the scanning;

means for extracting the outline of the cardiac muscle from the cardiac muscle's cross-sectional image data;

means for assuming a dilation/contraction of the cardiac muscle on the basis of the outline of the cardiac muscle extracted; and compensating means for compensating the motion velocity data on the basis of the assumed dilation/contraction direction.

19. A memory storing a computer-executable program code, the program code comprising:

means for causing the computer to input tissue cross-sectional image data relating to a cross-section of the inside of a subject and motion velocity data relating to an organ-of-interest in the subject;

means for causing the computer to extract an outline of the organ-of-interest from the tissue cross-sectional image data;

means for causing the computer to assume the motion direction of the organ-of-interest on the basis of the outline of the organ-of-interest; and means for causing the computer to compensate the motion velocity data on the basis of the assumed motion velocity.

* * * * *